United States Patent
Hussein et al.

(10) Patent No.: US 7,493,167 B2
(45) Date of Patent: Feb. 17, 2009

(54) MAGNETICALLY SHIELDED AIMD HOUSING WITH WINDOW FOR MAGNETICALLY ACTUATED SWITCH

(75) Inventors: Haytham Hussein, Woodstock, MD (US); Christine A. Frysz, Marriottsville, MD (US); Robert A. Stevenson, Canyon Country, CA (US)

(73) Assignee: Greatbatch-Sierra, Inc., Carson City, NV (US)

(*) Notice: Subject to any disclaimer, the term of this patent is extended or adjusted under 35 U.S.C. 154(b) by 715 days.

(21) Appl. No.: 11/163,848

(22) Filed: Nov. 1, 2005

(65) Prior Publication Data

US 2006/0217792 A1    Sep. 28, 2006

Related U.S. Application Data

(60) Provisional application No. 60/594,240, filed on Mar. 22, 2005.

(51) Int. Cl.
*A61N 1/375* (2006.01)
(52) U.S. Cl. .......................................... 607/36; 607/63
(58) Field of Classification Search ............. 607/30–33, 607/36–38, 59–61; 128/897–899, 903, 904, 128/908
See application file for complete search history.

(56) References Cited

U.S. PATENT DOCUMENTS

| | | | |
|---|---|---|---|
| 5,217,010 A | 6/1993 | Tsitlik et al. | |
| 5,527,348 A * | 6/1996 | Winkler et al. | 607/30 |
| 5,540,959 A | 7/1996 | Wang | |
| 5,749,910 A * | 5/1998 | Brumwell et al. | 607/36 |
| 6,506,972 B1 | 1/2003 | Wang | |
| 6,673,999 B1 | 1/2004 | Wang et al. | |
| 6,713,671 B1 | 3/2004 | Wang et al. | |
| 6,760,628 B2 | 7/2004 | Weiner et al. | |
| 6,765,144 B1 | 7/2004 | Wang et al. | |
| 6,815,609 B1 | 11/2004 | Wang et al. | |
| 6,829,509 B1 | 12/2004 | MacDonald et al. | |
| 6,850,803 B1 * | 2/2005 | Jimenez et al. | 607/61 |
| 6,901,290 B2 | 5/2005 | Foster et al. | |
| 7,174,212 B1 * | 2/2007 | Klehn et al. | 607/36 |
| 7,337,003 B2 * | 2/2008 | Malinowski | 607/36 |
| 2005/0113886 A1 * | 5/2005 | Fischell et al. | 607/60 |

* cited by examiner

*Primary Examiner*—Kennedy J Schaetzle
*Assistant Examiner*—Jessica Reidel
(74) *Attorney, Agent, or Firm*—Kelly Lowry & Kelley LLP

(57) ABSTRACT

An active implantable medical device (AIMD) having a magnetic shield on its housing for shielding the interior of the device from magnetic fields originating outside the housing. The magnetic shield is created using a magnetic absorbing coating on the inner surface of the housing. The AIMD includes an area of the housing left without the magnetic shield, a magnetic window, adjacent to a magnetically actuated device located inside of the housing. The magnetic window permits activation of the magnetically actuated device.

33 Claims, 4 Drawing Sheets

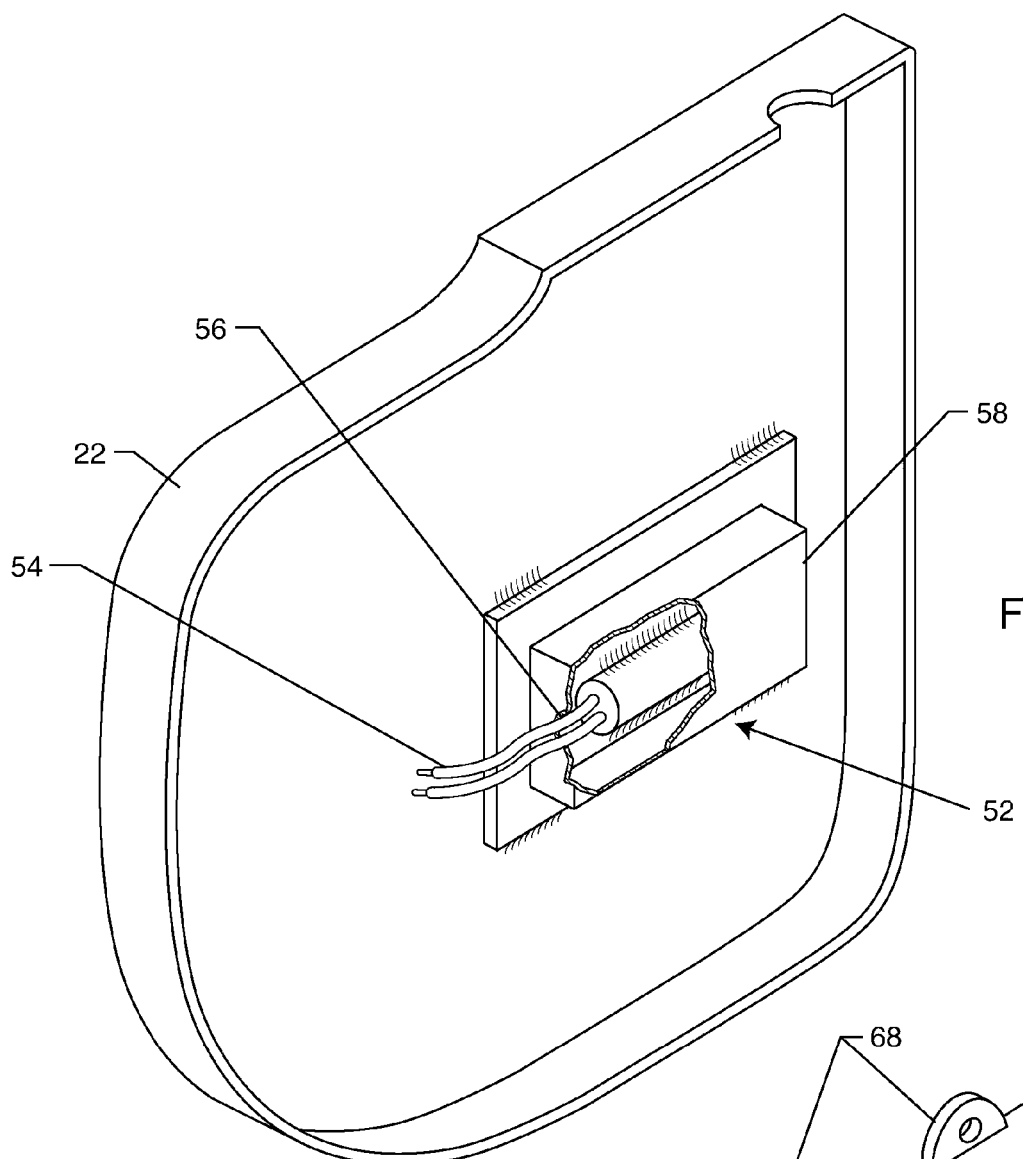
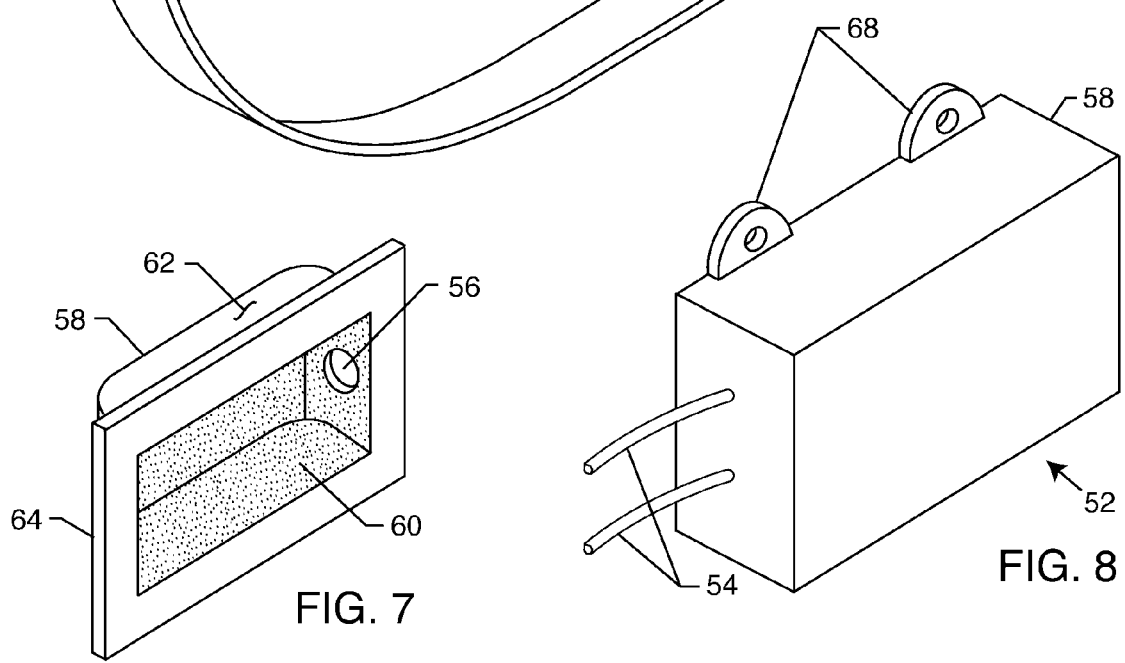

MAGNETICALLY SHIELDED AIMD HOUSING WITH WINDOW FOR MAGNETICALLY ACTUATED SWITCH

FIELD OF THE INVENTION

The present invention generally relates to active implantable medical devices (AIMDs) which include electrical and magnetic shielding. More particularly, the present invention relates to housings for AIMDs that are constructed from materials and/or have coatings that provide magnetic and electrical shielding to internal circuits. In addition, the housings include a window through a portion of the magnetic shielding permitting actuation of a reed switch, Hall-effect embedded telemetry coil, or other magnetically actuated device by interaction with a static magnet.

BACKGROUND OF THE INVENTION

The circuitry of most AIMDs is susceptible to the magnetic fields generated by magnetic resonance imaging (MRI) machines or other devices that generate magnetic fields similar to MRI machines. Thus, certain patients with AIMDs are not capable of undergoing an MRI procedure. Without proper shielding, such magnetic fields would interfere and possibly render the circuitry in the AIMD's inoperable.

There are a number of patents that discuss compatibility with MRI machines and the need for compatibility of AIMDs with magnetic fields such as those generated by MRI machines. These patents cover a wide variety of topics, including the need to protect implanted lead wires, as well as the need to protect AIMDs, such as cardiac pacemakers. U.S. Pat. No. 5,217,010, assigned to the Johns Hopkins University, describes a number of embodiments regarding electrically shielded housings. FIG. 17 of U.S. Pat. No. 5,217,010 illustrates such a housing, which consists of composite layers 302, 304, and describes the shield assembly as being a continuous non-magnetic metal case that prevents currents from being induced inside the internal pacemaker circuitry. All present titanium housings perform this function. The shielded housing disclosed in U.S. Pat. No. 5,217,010 is either a single layer or consists of laminates as shown in FIG. 17 where the laminated housing contains alternating metal and insulating layers. U.S. Pat. No. 5,217,010 describes FIG. 17 having metal layers 302, 306 and 310 and insulating layers 304, 308 and 312. According to U.S. Pat. No. 5,217,010, this embodiment reduces heating and other interference with proper pacemaker function caused by current flowing between pacemakers/sensing electrodes and the case of the pacemaker. The laminated housing divides up the pre-existing titanium case into separated layers thereby reducing current losses in the presence of a strong magnetic field. The primary objective of the structure in U.S. Pat. No. 5,217,010 is to reduce heating of the housing during exposure to magnetic fields. Some studies have indicated that the amount of heating is not generally an issue with present MRI technology. Accordingly, some degree of heating is acceptable, even desirable, in order to prevent the MRI field energy from reaching sensitive circuits within the AIMD. It is desirable not to have the shielded housing of the AIMD heat up more than about 2° C.-3° C. during an MRI procedure. A temperature rise of more than 3° C. could become quite uncomfortable for the patient and may cause damage to adjacent tissues.

Accordingly, a methodology is desired to apply a magnetic shield coating of various densities and various magnetic and material properties and to control its thickness such that only an acceptable amount of heating is permitted, but not so much heating as to cause discomfort or damage to patient tissue. There are a number of other patents that describe magnetic shielding, shielded conductors or housings that include: U.S. Pat. Nos. 6,506,972; 5,540,959; 6,673,999; 6,713,671; 6,760,628; 6,765,144; 6,815,609; 6,829,509; and 6,901,290.

U.S. Pat. No. 6,506,972 describes magnetically shielded conductor assemblies covered with a nanomagnetic material as described in the patent. There is nothing in U.S. Pat. No. 6,506,972 that describes the coating or shielding of the housing of an active implantable medical device. U.S. Pat. No. 5,540,959 describes a process for preparing a coated substrate in which a mist of particles is created. U.S. Pat. No. 6,673,999 is a Continuation-in-Part of U.S. Pat. No. 6,506,972, which is directed toward the coating and protection of leads and related assemblies.

U.S. Pat. No. 6,713,671 describes a shielded assembly containing a substrate and a shield. It primarily describes a magnetic shielding coating. As shown in FIG. 1a of U.S. Pat. No. 6,713,671, there is a nanomagnetic material coating, a heat treatment and then a coating of insulator material. In FIG. 29 a composite shield assembly that shields from magnetic and/or electric fields is shown. A number of materials are also described. In column 28, line 35 and column 30, line 55, U.S. Pat. No. 6,713,671 describes the various features. The description of the shield 3004 is that it is "disposed above the substrate 3002. As used herein, the term 'above' refers to a shield that is disposed between a source 3006 of electromagnetic radiation and the substrate 3002. The shield 3004 is comprised of from about 1 to about 99 weight percent of nanomagnetic material 3008; such nanomagnetic material, and its properties are described elsewhere in this specification." Col. 28, line 65-Col. 29, line 4. Column 29, lines 9-17, states "[r]eferring again to FIG. 29, and in the preferred embodiment depicted therein, it will be seen that the shield 3004 is also comprised of another material 3010 that preferably has an electrical resistivity of from about 1 microhm-centimeter to about $1 \times 10^{25}$ microhm-centimeters. This material 3010 is preferably present in the shield at a concentration of from about 1 to about 99 weight percent, and more preferably, from about 40 to about 60 weight percent." The patent goes on to further describe said material 3010 as a carbon nanotube material.

U.S. Pat. No. 6,760,628 is primarily directed to a shielded fiber optic system that is addressed to MRI. U.S. Pat. No. 6,765,144 describes an assembly for shielding implantable medical devices from the effects of high frequency radiation and from MRI signals. The assembly includes an implanted medical device and a magnetic shield composed of nanomagnetic material disposed between the medical device and the high frequency radiation. U.S. Pat. No. 6,765,144 describes FIGS. 24, 25 and 26 as depicting a layered magnetic shield using various nano-materials. However, U.S. Pat. No. 6,765,144 does not disclose a continuous metallic electromagnetic shield as part of its assembly. U.S. Pat. No. 6,815,609 is very similar to U.S. Pat. No. 6,765,144, in that a magnetically shielded substrate assembly includes a substrate and a magnetic shield disposed over the substrate. The above comments pertaining to U.S. Pat. No. 6,765,144 also apply to U.S. Pat. No. 6,815,609.

U.S. Pat. No. 6,829,509 discloses an electromagnetic immune tissue invasive system which is primarily a fiber optic system with some description of electrically shielded electrical lead system. None of the features of U.S. Pat. No. 6,829,509 are practical in the context of the present invention.

U.S. Pat. No. 6,901,290 discloses an electromagnetic immune tissue invasive system that includes control circuits contained within a primary housing having an electromagnetic shield. The shield disclosed in U.S. Pat. No. 6,901,290 is a metallic sheath, a carbon composite sheath, or a polymer composite sheath the purpose of which is to shield the primary device housing and any circuits therein from electromagnetic interference. Alternatively, the lead system may comprise a plurality of electrical leads, each lead having a similar shield therearound to prevent the electrical leads from conducting stray electromagnetic interference. In addition to the shield or in lieu of the shield, each electrical lead may include an electrical filter that comprises capacitive and inductive filter elements adapted to filter out predetermined frequencies of electromagnetic interference. In either embodiment, the shield has a biocompatible surface such as a non-permeable diffusion resistant biocompatible material. The shield can be formed of various composite materials so as to provide an electromagnetic shield around the primary housing. Examples of such materials are metallic shielding or polymer or carbon composites such as carbon fullerenes.

Accordingly, an AIMD with improved magnetic and electrical shielding is needed that is simpler in design and construction so as to require less space and expense while properly shielding internal circuitry from electric and magnetic fields and permitting the intentional actuation of a reed switch, Hall-effect device, embedded telemetry coil or other magnetically actuated device within such AIMD. The disclosed invention fulfills these needs and provides other related advantages.

SUMMARY OF THE INVENTION

The present invention is directed to active implantable medical devices (AIMDs) having improved shielding against magnetic fields. Specifically, the present invention is an AIMD comprising a housing having a terminal through which a lead wire extends, a magnetically actuated device disposed within the housing, and a magnetic shield disposed adjacent to the housing for shielding an interior of the housing from magnetic fields originating exteriorly of the housing, the magnetic shield including a window adjacent to the magnetically actuated device. The housing comprises a material providing electrical shielding, i.e., titanium.

The magnetic shield comprises a coating applied to interior surfaces of the housing. The coating comprises ferrous paint, nickel plating, nickel coating, nano-materials, Mu-metal materials, or a sogel or slurry of nano-materials containing magnetic dipoles. The magnetically actuated device is a reed switch, a Hall-effect device, an embedded telemetry coil, a low frequency telemetry coil, a close-coupled subcutaneous battery recharging circuit, or the like. A sub-housing overlays the magnetic shield window so that the magnetically actuated device is disposed between the window and the sub-housing. The sub-housing comprises an electrical shield, i.e., titanium, and includes a secondary magnetic shield comprising a coating applied to the interior surfaces of the sub-housing. As with the magnetic shield coating, the secondary magnetic shield coating comprises ferrous paint, nickel plating, nickel coating, nano-materials, Mu-metal materials, or a sogel or slurry of nano-materials containing magnetic dipoles.

The terminal comprises an insulator through which the lead wire extends, and a terminal magnetic shield. The terminal magnetic shield comprises non-magnetic electrodes within the insulator, the non-magnetic electrodes comprising nickel electrodes.

The AIMD comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

These and other aspects of the invention will be apparent to one skilled in the art in light of the following detailed description of the preferred embodiments.

BRIEF DESCRIPTION OF THE DRAWINGS

The accompanying drawings illustrate the invention. In such drawings:

FIG. 6 is an isometric view of one of the halves of the housing shown in FIG. 2 including an attached magnetically actuated device over the magnetic window and a cut-open view of the sub-housing on such device.

FIG. 7 is an isometric view of the inside an alternative embodiment for the sub-housing cover of a magnetically actuated device for use in the present invention.

FIG. 8 is an isometric view an alternative embodiment of the sub-housing for a magnetically actuated device for use in the present invention.

DETAILED DESCRIPTION OF THE PREFERRED EMBODIMENT

The present invention is directed to active implantable medical devices (AIMDs) such as a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device. The housings of such AIMDs are constructed from materials and/or have coatings that provide magnetic and electrical shielding to internal components in the AIMDs. In addition, the housings include an unshielded area or window, through a portion of the magnetic shielding permitting the passage of magnetic fields to activate a reed switch, a Hall-effect device, an embedded telemetry coil, a low frequency telemetry coil, a close coupled subcutaneous battery recharging circuit, or other magnetically actuated device by interaction with a static magnet.

Figure 1:
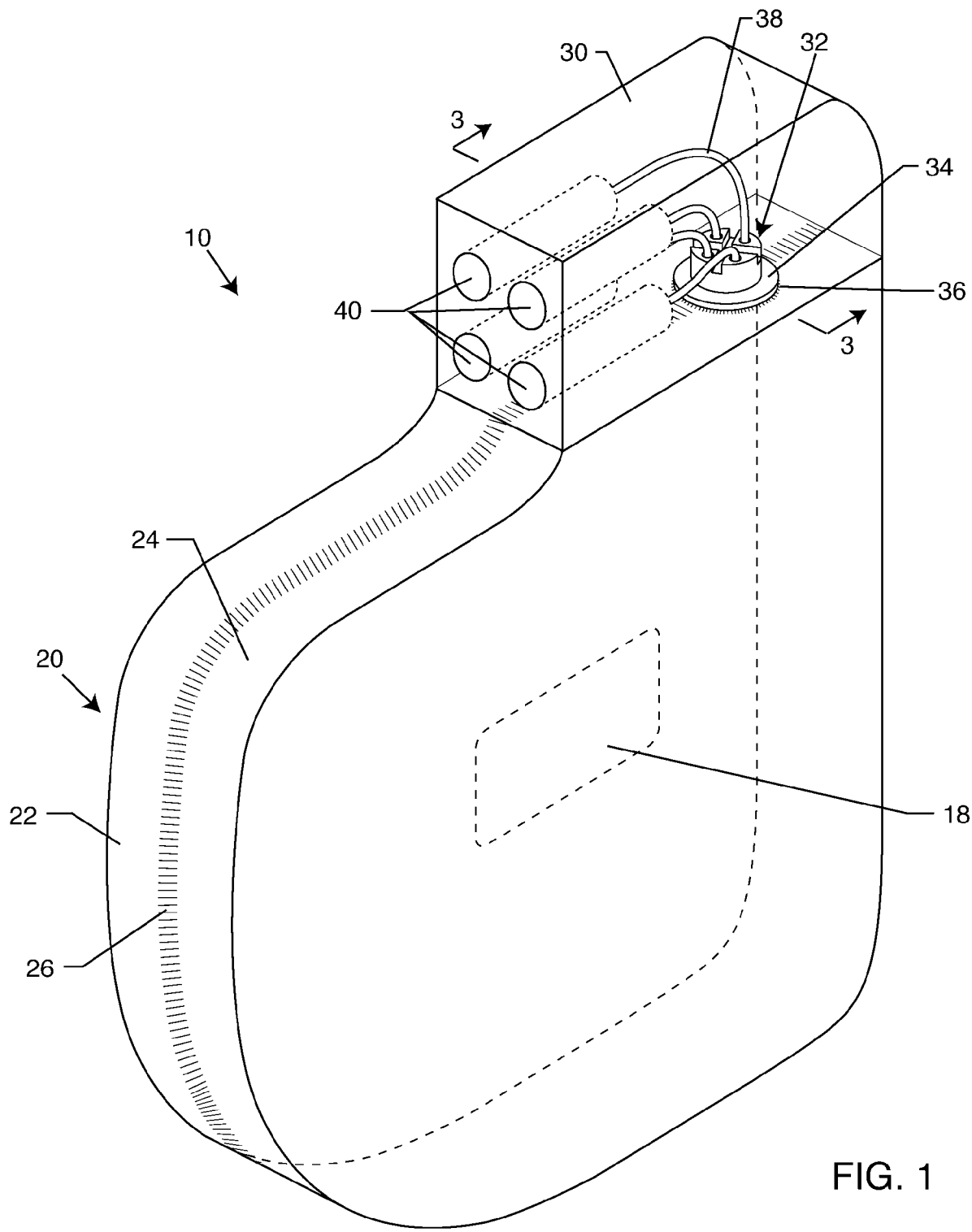
FIG. 1 is an isometric view of an AIMD having a housing and a connector block according to the present invention.

FIG. 1 is an isometric view of a typical AIMD 10 having an AIMD housing 20 and a connector housing 30. The AIMD housing 20 may comprise a single unit or, as depicted in FIG. 1, may be comprised of two halves 22, 24 which are laser welded together to hermetically enclose the various electronic circuits within. The AIMD housing 20 is typically of titanium, stainless steel, ceramic or other biocompatible material. As in most AIMDs in use today, the AIMD housing 20 is comprised of titanium and the halves 22, 24 are joined by a hermetic weld seam 26, as shown.

The AIMD housing 20 is distinguishable from the prior art, including those disclosed in U.S. Pat. Nos. 5,217,010, 6,713,671 and 6,901,290. The AIMD housing 20 begins with the known shields, i.e., a titanium, stainless steel or similar housing where the continuous metallic surface provides shielding against high frequency electrical fields. However, the AIMD housing 20 introduces a bi-layer electric and magnetic shield assembly created by the addition of a novel magnetic shield coating 28 to the inner surface of the AIMD housing 20. This may incorporate a number of alternating layers; however, because of the extreme process associated with such techniques, the preferred embodiment includes only one electrical shield layer and one magnetic shield layer.

Referring once again to FIG. 1, there is a hermetic terminal 32, which is well known in the art, that is laser welded (see seam 36) by its ferrule 34 to the AIMD housing 20. FIG. 1 depicts a quad polar feedthrough terminal 32 with lead wires 38 to a common IS-1, DF-1 or IS-4 connector block 40. The number of lead wires 38 are an example only and can vary anywhere from 1 to 8 to 12 or even more.

As described, it is desirable to have both electric and magnetic shielding in the AIMD housing 20. Specifically, the inventive shielding resides in a composite or dual-layer shield in the AIMD housing 20 providing both electric and magnetic shielding. The electric shield has a very low electrical resistivity and is generally metallic. That is, it provides excellent immunity to high frequency emitters that might come from microwave ovens, cellular telephones and the like. It is well known in the art that an AIMD housing 20 manufactured from titanium or other materials with similar properties, provides the desired resistance to high frequency electrical fields. Other materials with similar properties include materials that generally have an electrical resistivity from about 0.001 microhm-centimeters to about $1 \times 10^4$ microhm-centimeters. The second part of the inventive shield, the magnetic shield 28, generally has properties with a saturation magnetization of about 0.5 to about 40,000 gauss, a coercive force to about 0.001 to about 10,000 orsteds, a relative magnetic permeability from about 0.18 to about 600,000 and various average particle sizes. One such material, for example, is described by U.S. Pat. No. 6,713,671, as well as others.

However, AIMDs may also be exposed to and damaged by low frequency or static magnetic fields. As described herein, magnetic resonance imaging (MRI) devices produce very powerful low frequency or static magnetic fields. A titanium housing, which is common in the prior art, is transparent to such magnetic fields and provides no protection to the internal circuits of the AIMD. Accordingly, it is a novel feature to provide a magnetic shield 28 on the AIMD housing 20 that includes a magnetic shielding and/or magnetic absorbent material. Such materials can include ferrous paints wherein paint that contains magnetic particles such as nickel, nano-materials, Mu-metal materials or the like, are applied by coating, plating, spraying, silk screening, or the like. The magnetic shield 28 may also be applied as a sogel or slurry of nano-materials containing magnetic dipoles.

In all of the above methods, the magnetic shield 28 would generally be applied to the inside of the AIMD housing 20 since nickel and other ferrous metals are generally not biocompatible. That is, they need to be protected from exposure to body fluids the same as the other sensitive electronic components contained within the AIMD 10. However, the invention also contemplates placing such magnetic shields 28 on the outside of the housing 20. In addition, this invention also contemplates the use of alternating shielding layers providing resistance to electric and magnetic fields. However, this specification describes the preferred embodiment which uses a bi-layer construct comprising a titanium AIMD housing 20 for electrical resistance and a novel magnetic shield 28 for magnetic resistance. The disclosures of U.S. Pat. Nos. 5,540,959, 6,673,999, and 6,765,144 are hereby incorporated as a number of methods that could be used to prepare a magnetic shield 28 for the AIMD housing 20.

The application of the magnetic shield 28 may be varied in composition, density, thickness of application, and other various magnetic and material properties to control the effectiveness of the magnetic resistance. The variation of the above-mentioned properties is intended to have the effect of absorbing some of the incident magnetic fields 66 thereby creating some degree of heating in the AIMD housing 20. The fact that the incident magnetic fields are absorbed by the AIMD housing 20 prevents the incident magnetic field energy 66 from reaching sensitive circuits within the device 10.

It is desirable to limit heating of the housing 20 to no more than 2° C. to 3° C. during an MRI procedure. A temperature increase of more than 2° C. to 3° C. may result in discomfort to the patient and may cause damage to adjacent body tissue. By employing a magnetic absorbing material as the magnetic shield 28, the AIMD housing 20 deliberately generates some heat in the device 10. The methodology of varying the thickness and composition of the magnetic shield 28 results in a controlled amount of heating of the AIMD housing 20 during an MRI procedure or exposure to similar magnetic fields.

Figure 2:
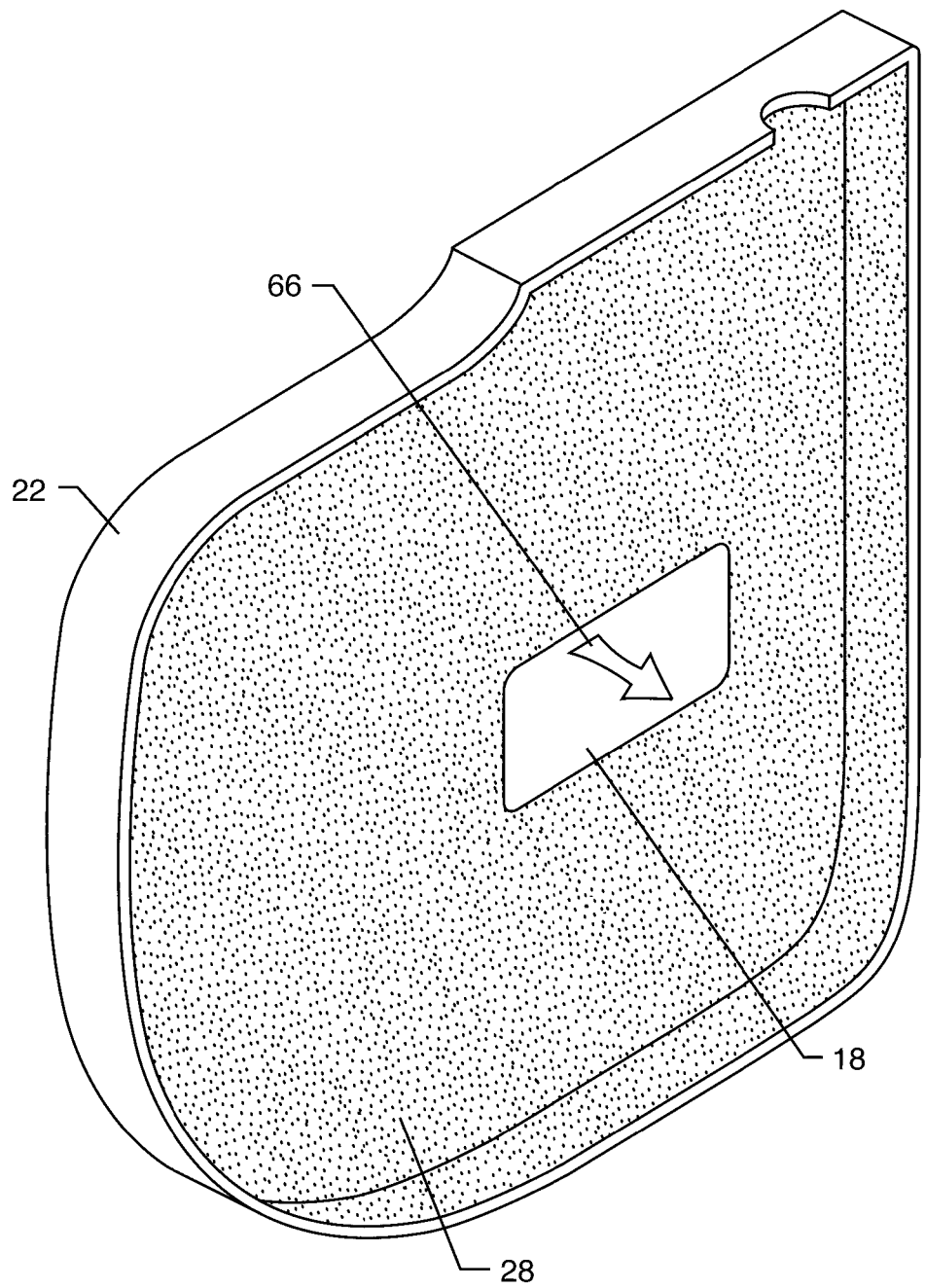
FIG. 2 is an isometric view of one of the halves of the housing having a magnetic coating and window according to the present invention.

Referring to FIG. 2, one can better understand the application of the magnetic shield 28 to the inside of the AIMD housing 20 (the first half 22 is shown—the second half 24 is not shown). The magnetic shield 28 is intended to cover the entire inner surface of the AIMD housing 20 or its halves 22, 24. In FIGS. 1, 2 and 6, a portion of the AIMD housing 20 does not have the magnetic shield 28, resulting in an unshielded portion or window 18 through the magnetic shield 28. The window 18 may be anywhere on the AIMD housing 20 or either half 22, 24. For purposes of this description, the window 18 will be described as part of the first half 22. This window 18 is important to permit communication with a magnetically actuated device 52, such as a reed switch or similar device—typically included in cardiac pacemakers and implantable cardioverter defibrillators (ICDs) or other AIMDs. Other magnetically actuated devices 52 include Hall-effect devices, embedded telemetry coils, low frequency telemetry coils, close coupled subcutaneous battery charging circuits, or the like.

Many AIMDs incorporate such a magnetically actuated device 52 wherein a doctor, emergency medical technician or even the patient can place a static magnet over the AIMD and cause the magnetically actuated device 52 to activate, i.e., close a reed switch. The actuation of a magnetically actuated device 52 such as a reed switch causes a pacemaker to switch to what is known as asynchronous pacing or fixed rate pacing mode.

Accordingly, it is very important that when magnetic shielding of an AIMD housing 20 is contemplated, provision must be made so that the magnetically actuated device 52 may still be actuated. In addition to reed switches for pacemakers and ICDs, there are other AIMDs that may include magnetically actuated devices 52 that require actuation through exposure to a magnetic field. Accordingly, the magnetic window 18 as described herein is not limited to communication with reed switches—it can prove useful for a variety of applications that should be obvious to those skilled in the art.

Provision of a window 18 in the shielded AIMD housing 20 is problematic in that this provides a passageway through the magnetic shield 28 of the AIMD housing 20 where magnetic fields, from MRI procedures or otherwise, may enter into the AIMD housing 20 and reach the internal circuits sensitive to such magnetic fields and disrupt, overheat, or even damage certain circuits.

FIG. 6 illustrates the first half 22 that was previously described with a magnetically actuated device 52 shown bonded directly over the magnetic window 18. The cut open view of the magnetically actuated device 52 depicts two lead wires 54 exiting the device 52. There is a hole 56 provided in a stamped or formed sub-housing 58 so that the lead wires 54 can ingress and egress from the magnetically actuated device 52 to the other electronic circuits of the AIMD 10. It is important that the sub-housing 58 have a magnetic shield 60 similar to the AIMD housing 20. It is also important that the sub-housing 58 have electric shielding similar to the AIMD housing 20. Failure to provide either would mean that the AIMD 10 would become sensitive to either high frequency electric or low frequency magnetic fields.

Accordingly, it is also novel that the sub-housing 58 enclosing the magnetically actuated device 52 and covering the magnetic window 18, as shown in FIG. 6, incorporates all of the shielding features set forth above for the AIMD housing 20. That is, the sub-housing 58 is preferably of a metal such as titanium, stainless steel, copper or the like which has been coated with a magnetic shield 60 as described. It is also possible to replace the metal (titanium, stainless steel, copper or the like) with a plastic that has an electric shield 62 which is well known in the art in addition to the magnetic shield 60. Such electric 62 and magnetic 60 shields may be applied one on top of the other on either the inside or the outside of the sub-housing 58.

Referring now to FIG. 7, one can see a blown-up view of an alternate embodiment that provides a magnetic 60 and electric 62 shielded sub-housing 58 for covering a magnetically actuated device 52 which is separate from the device 52. The hole 56 for passage of lead wires 54 and mounting flange 64 for convenient attachment to the AIMD housing 20 is clearly visible. The sub-housing 58 is designed to be placed over the magnetic window 18 as previously described. The electric 62 and magnetic 60 shields may be of a variety of materials as previously described. The mounting flange 64 may be a variety of sizes and shapes or not be present at all. The mounting flange 64 as depicted is a convenient method of making attachment between the sub-housing 58 and the AIMD housing 20. Attachment may be by laser welding, brazing, thermal setting non-conductive or conductive adhesives, solders, mechanical fasteners, or the like. It will be obvious to those skilled in the art that there are many ways of making this attachment.

FIG. 8 illustrates an alternative embodiment which eliminates the need for a separate sub-housing 58 having magnetic 60 and electric 62 shields as previously described in FIG. 7. FIG. 8 depicts a magnetically actuated device 52 wherein the sub-housing 58 is integral with the device 52 and provides both electric 62 and magnetic 60 shields. In this embodiment, attachment of the magnetically actuated device 52 over the magnetic window 18 achieves the desired shielding. The magnetically actuated device 52 may be exposed to an incident magnetic field, for example, from a magnet held externally over an AIMD.

Accordingly, referring back to FIG. 2, the magnetic field 66 can directly impinge upon the backside of the sub-housing 58 shown in FIG. 8. The backside, which is the side that abuts against the magnetic window 18, specifically does not have the magnetic shield 60. It may or may not have an electric shield 62. However, it is very important that the magnetic field 66 be able to reach the magnetically actuated device 52 in order to activate it. It is also very important that all of the surfaces other than the backside of the sub-housing 58 have both electric 62 and magnetic 60 shields. Accordingly, the magnetically actuated device 52 which has a shielded sub-housing 58, may accomplish the goals of the inventive device in an integrated package. That is, it permits a magnetically actuated device 52 to be placed over the magnetic window 18, but it also has the desired function of ensuring that the rest of the components within the AIMD 10 are protected from both electric and magnetic fields 66. It will be obvious to those skilled in the art that various mounting means 68 for the integrated assembly of FIG. 8 may be employed and it may also take on various sizes, shapes and materials.

Figure 3:
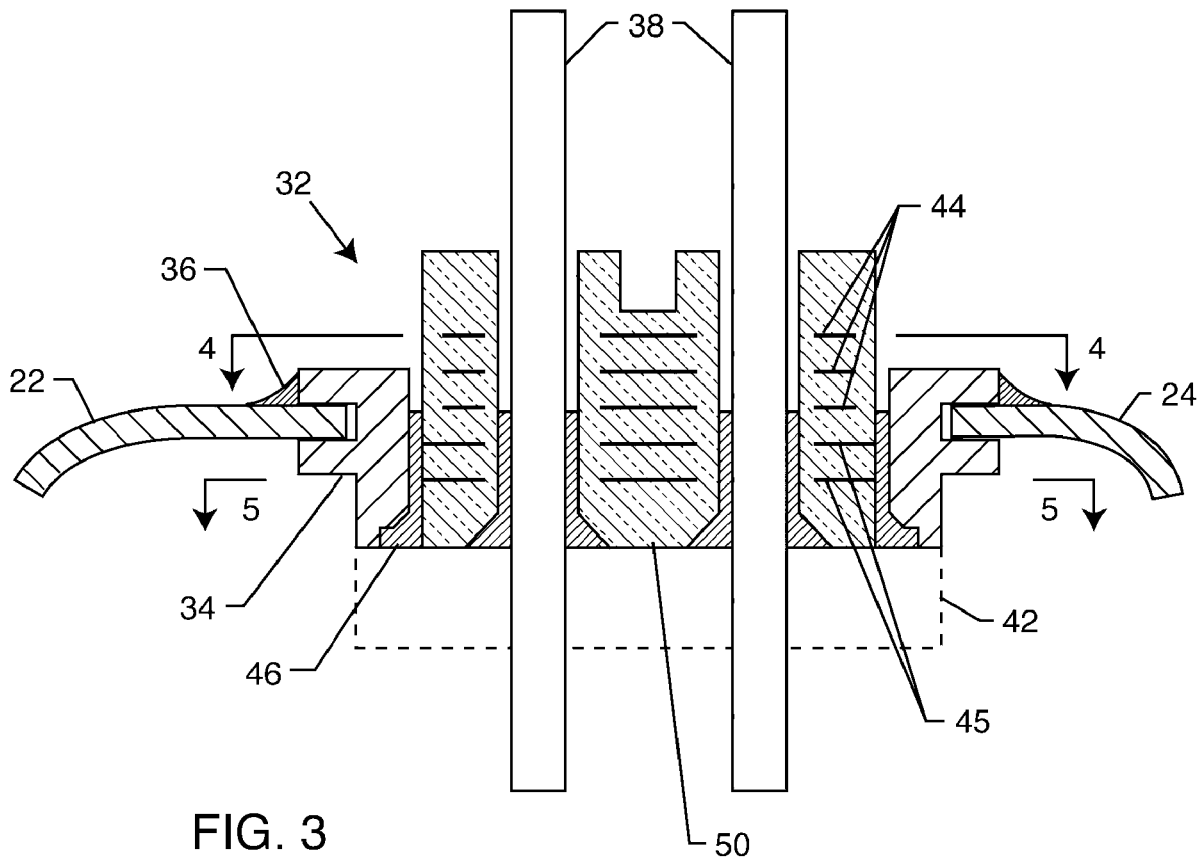
FIG. 3 is a cross-section of a terminal installed in an AIMD of the present invention including an insulator.

FIG. 3 depicts a cross-section of the novel magnetically shielded terminal 32 previously shown in FIG. 1. Referring to the cross-section, the narrow-embedded nickel or equivalent ferrous electrodes 44 are shown. The ceramic or glass insulator 50 of the terminal 32 completely surrounds the embedded nickel electrodes 44 such that they do not contact bodily fluids. The reason for this is that nickel is generally not considered a biocompatible material. However, wide-embedded nickel electrodes 45 go to the outside diameter or perimeter of the ceramic or glass insulator 50. The reason that this is permitted is that the gold braze material 46 covers the exposed portion thereof and protects the wide embedded electrodes 45 from exposure to bodily fluids. It should also be noted that unlike an electric shield, it is not important that the nickel electrodes 44 and 45 form a continuous overall shield and communicate electrically with the AIMD housing 20. That is, an incident magnetic field is attenuated by the simple action of the magnetic dipoles embedded within the nickel or equivalent material electrodes 44 and 45. The purpose of the electrodes 44 and 45 is not to provide capacitance. The electrodes 44 and 45 provide magnetic shielding against an incident static or low frequency magnetic field and assist the magnetically shielded AIMD housing 20 in protecting the internal electronic circuits of the device 10 from magnetic fields such as those produced by an MRI device.

Figure 4:
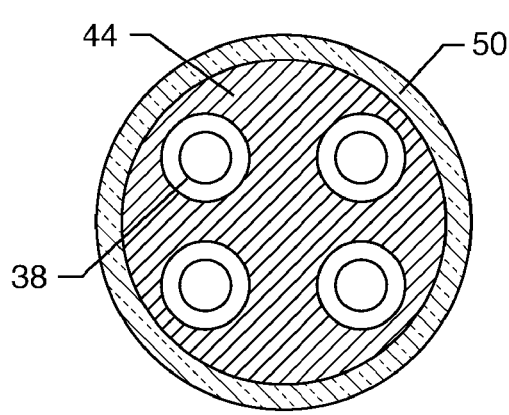
FIG. 4 is a cross-section of the terminal shown in FIG. 3 depicting magnetic shield electrode plates embedded within the insulator.
Figure 5:
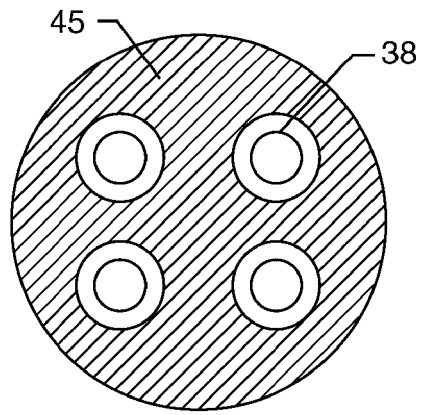
FIG. 5 is a cross-section of the terminal shown in FIG. 3 depicting magnetic shield electrode plates reaching the edge of the insulator.

The novel electrodes 44 and 45 are more clearly shown in FIGS. 4 and 5. FIG. 4 illustrates the novel electrodes 44 in relation to the ceramic/glass insulator 50. FIG. 5 illustrates the novel electrodes 45 that are protected from body fluid by the gold brazed material 46. It is well known in the art that an electromagnetic interference (EMI) filter capacitor 42 may be mounted on the inside and integral with the terminal 32 to assist in shielding against high frequency electric fields.

Although various embodiments have been described in detail for purposes of illustration, various modifications may be made without departing from the scope and spirit of the invention.

What is claimed is:

1. An active implantable medical device, comprising:
    a housing having a terminal through which a lead wire extends;
    a magnetically actuated device disposed within the housing; and
    a magnetic shield disposed adjacent to the housing for shielding an interior of the housing from magnetic fields originating exteriorly of the housing, the magnetic shield including a window adjacent to the magnetically actuated device, and wherein the magnetic shield comprises a coating applied to interior surfaces of the housing.

2. The active implantable medical device of claim 1, wherein the coating comprises ferrous paint, nickel plating, nickel coating, nano-materials, Mu-metal materials, or a sogel or slurry of nano-materials containing magnetic dipoles.

3. The active implantable medical device of claim 1, wherein the magnetically actuated device is a reed switch, a Hall-effect device, an embedded telemetry coil, a low frequency telemetry coil, or a close-coupled subcutaneous battery recharging circuit.

4. The active implantable medical device of claim 1, including a sub-housing for the magnetically actuated device, the sub-housing overlaying the magnetic shield window so that the magnetically actuated device is disposed between the window and the sub-housing.

5. The active implantable medical device of claim 4, including a secondary magnetic shield disposed adjacent to the sub-housing.

6. The active implantable medical device of claim 5, wherein the secondary magnetic shield comprises a coating applied to interior surfaces of the sub-housing.

7. The active implantable medical device of claim 6, wherein the secondary magnetic shield coating comprises ferrous paint, nickel plating, nickel coating, nano-materials, Mu-metal materials, or a sogel or slurry of nano-materials containing magnetic dipoles.

8. The active implantable medical device of claim 4, wherein the sub-housing comprises an electrical shield.

9. The active implantable medical device of claim 1, wherein the terminal comprises an insulator through which the lead wire extends, and a terminal magnetic shield.

10. The active implantable medical device of claim 9, wherein the terminal magnetic shield comprises non-magnetic electrodes within the insulator.

11. The active implantable medical device of claim 10, wherein the non-magnetic electrodes comprise nickel electrodes.

12. The active implantable medical device of claim 1, wherein the housing comprises an electrical shield.

13. The active implantable medical device of claim 12, wherein the electrical shield comprises titanium.

14. The active implantable medical device of claim 1, wherein the AIMD comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

15. An active implantable medical device, comprising:
a housing having a terminal through which a lead wire extends, wherein the housing comprises an electrical shield;
a magnetically actuated device disposed within the housing;
a magnetic shield disposed adjacent to the housing for shielding an interior of the housing from magnetic fields originating exteriorly of the housing, the magnetic shield including a window adjacent to the magnetically actuated device;
a sub-housing for the magnetically actuated device, the sub-housing overlaying the magnetic shield window so that the magnetically actuated device is disposed between the window and the sub-housing; and
a secondary magnetic shield disposed adjacent to the sub-housing.

16. The active implantable medical device of claim 15, wherein the magnetic shield and the secondary magnetic shield comprise coatings applied to interior surfaces of the housing and the sub-housing.

17. The active implantable medical device of claim 16, wherein the coatings comprise ferrous paint, nickel plating, nickel coating, nano-materials, Mu-metal materials, or a sogel or slurry of nano-materials containing magnetic dipoles.

18. The active implantable medical device of claim 16, wherein the magnetically actuated device is a reed switch, a Hall-effect device, an embedded telemetry coil, a low frequency telemetry coil, or a close-coupled subcutaneous battery recharging circuit.

19. The active implantable medical device of claim 15, wherein the terminal comprises an insulator through which the lead wire extends, and a terminal magnetic shield.

20. The active implantable medical device of claim 19, wherein the terminal magnetic shield comprises non-magnetic electrodes within the insulator.

21. The active implantable medical device of claim 20, wherein the non-magnetic electrodes comprise nickel electrodes.

22. The active implantable medical device of claim 15, wherein the sub-housing comprises an electrical shield.

23. The active implantable medical device of claim 22, wherein the electrical shields comprise titanium.

24. The active implantable medical device of claim 15, wherein the AIMD comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

25. An active implantable medical device, comprising:
a housing having a terminal insulator through which a lead wire extends, and a terminal magnetic shield;
a magnetically actuated device disposed within the housing;
a magnetic shield disposed adjacent to the housing for shielding an interior of the housing from magnetic fields originating exteriorly of the housing, the magnetic shield including a window adjacent to the magnetically actuated device;
a sub-housing for the magnetically actuated device, the sub-housing overlaying the magnetic shield window so that the magnetically actuated device is disposed between the window and the sub-housing; and
a secondary magnetic shield disposed adjacent to the sub-housing.

26. The active implantable medical device of claim 25, wherein the AIMD comprises a cardiac pacemaker, an implantable defibrillator, a congestive heart failure device, a hearing implant, a cochlear implant, a neurostimulator, a drug pump, a ventricular assist device, an insulin pump, a spinal cord stimulator, an implantable sensing system, a deep brain stimulator, an artificial heart, an incontinence device, a vagus nerve stimulator, a bone growth stimulator, a gastric pacemaker, or a prosthetic device.

27. The active implantable medical device of claim 26, wherein the magnetic shield and the secondary magnetic shield comprise coatings applied to interior surfaces of the housing and the sub-housing.

28. The active implantable medical device of claim 27, wherein the coatings comprise ferrous paint, nickel plating, nickel coating, nano-materials, Mu-metal materials, or a sogel or slurry of nano-materials containing magnetic dipoles.

29. The active implantable medical device of claim 26, wherein the magnetically actuated device is a reed switch, a Hall-effect device, an embedded telemetry coil, a low frequency telemetry coil, or a close-coupled subcutaneous battery recharging circuit.

30. The active implantable medical device of claim 25, wherein the terminal magnetic shield comprises non-magnetic electrodes within the insulator.

31. The active implantable medical device of claim 30, wherein the non-magnetic electrodes comprise nickel electrodes.

32. The active implantable medical device of claim 31, wherein the electrical shield comprises titanium.

33. The active implantable medical device of claim 25, wherein the housing and the sub-housing both comprise an electrical shield.

* * * * *